United States Patent
Tabuteau

(10) Patent No.: US 11,986,444 B2
(45) Date of Patent: *May 21, 2024

(54) TREATMENT OF POOR METABOLIZERS OF DEXTROMETHORPHAN WITH A COMBINATION OF BUPROPION AND DEXTROMETHORPHAN

(71) Applicant: ANTECIP BIOVENTURES II LLC, New York, NY (US)

(72) Inventor: Herriot Tabuteau, New York, NY (US)

(73) Assignee: Antecip Bioventures II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/488,366

(22) Filed: Oct. 17, 2023

(65) Prior Publication Data

US 2024/0050383 A1 Feb. 15, 2024

Related U.S. Application Data

(63) Continuation of application No. 18/169,571, filed on Feb. 15, 2023.

(60) Provisional application No. 63/357,471, filed on Jun. 30, 2022, provisional application No. 63/370,577, filed on Aug. 5, 2022, provisional application No. 63/370,769, filed on Aug. 8, 2022.

(51) Int. Cl.
*A61K 31/137* (2006.01)
*A61K 9/20* (2006.01)
*A61K 31/485* (2006.01)

(52) U.S. Cl.
CPC .......... *A61K 31/137* (2013.01); *A61K 9/2009* (2013.01); *A61K 9/2013* (2013.01); *A61K 9/2027* (2013.01); *A61K 9/2054* (2013.01); *A61K 9/2086* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 5,358,970 A | 10/1994 | Ruff et al. | |
| 5,731,000 A | 3/1998 | Ruff et al. | |
| 5,763,493 A | 6/1998 | Ruff et al. | |
| 6,306,436 B1 | 10/2001 | Chungi et al. | |
| 6,780,871 B2 | 8/2004 | Glick et al. | |
| 8,088,786 B2 | 1/2012 | Mckinney et al. | |
| 8,569,328 B1 | 10/2013 | Tabuteau | |
| 9,168,234 B2 | 10/2015 | Tabuteau | |
| 9,198,905 B2 | 12/2015 | Tabuteau | |
| 9,205,083 B2 | 12/2015 | Tabuteau | |
| 9,238,032 B2 | 1/2016 | Tabuteau | |
| 9,278,095 B2 | 3/2016 | Tabuteau | |
| 9,314,462 B2 | 4/2016 | Tabuteau | |
| 9,370,513 B2 | 6/2016 | Tabuteau | |
| 9,375,429 B2 | 6/2016 | Tabuteau | |
| 9,402,843 B2 | 8/2016 | Tabuteau | |
| 9,402,844 B2 | 8/2016 | Tabuteau | |
| 9,408,815 B2 | 8/2016 | Tabuteau | |
| 9,421,176 B1 | 8/2016 | Tabuteau | |
| 9,457,023 B1 | 10/2016 | Tabuteau | |
| 9,457,025 B2 | 10/2016 | Tabuteau | |
| 9,474,731 B1 | 10/2016 | Tabuteau | |
| 9,486,450 B2 | 11/2016 | Tabuteau | |
| 9,700,528 B2 | 7/2017 | Tabuteau | |
| 9,700,553 B2 | 7/2017 | Tabuteau | |
| 9,707,191 B2 | 7/2017 | Tabuteau | |
| 9,763,932 B2 | 9/2017 | Tabuteau | |
| 9,861,595 B2 | 1/2018 | Tabuteau | |
| 9,867,819 B2 | 1/2018 | Tabuteau | |
| 9,968,568 B2 | 5/2018 | Tabuteau | |
| 10,058,518 B2 | 8/2018 | Tabuteau | |
| 10,064,857 B2 | 9/2018 | Tabuteau | |
| 10,080,727 B2 | 9/2018 | Tabuteau | |
| 10,092,560 B2 | 10/2018 | Tabuteau | |
| 10,092,561 B2 | 10/2018 | Tabuteau | |
| 10,105,327 B2 | 10/2018 | Tabuteau | |
| 10,105,361 B2 | 10/2018 | Tabuteau | |
| 10,251,879 B2 | 4/2019 | Tabuteau | |
| 10,463,634 B2 | 11/2019 | Tabuteau | |
| 10,512,643 B2 | 12/2019 | Tabuteau | |
| 10,548,857 B2 | 2/2020 | Tabuteau | |
| 10,596,167 B2 | 3/2020 | Tabuteau | |
| 10,688,066 B2 | 6/2020 | Tabuteau | |

(Continued)

FOREIGN PATENT DOCUMENTS

| | | |
|---|---|---|
| BR | 102016010170 A2 | 11/2017 |
| EP | 4183391 A1 | 5/2023 |

(Continued)

OTHER PUBLICATIONS

Spravato (esketamine), Highlights of Prescribing Information, revised Jul. 2020.
Nuedexta (dextromethorphan hydrobromide and quinidine sulfate), Highlights of Prescribing Information, revised Dec. 2022.
Aplenzin (bupropion hydrobromide), Highlights of Prescribing Information, revised Mar. 2022.

(Continued)

*Primary Examiner* — Melissa S Mercier
(74) *Attorney, Agent, or Firm* — Procopio, Cory, Hargreaves & Savitch LLP; Brent A. Johnson; Yuefen Zhou

(57) ABSTRACT

Disclosed herein is a method of safely treating a nervous system condition with a combination of dextromethorphan and bupropion. This method is intended for patients having a neurological condition or a psychiatric condition, such as major depressive disorder, and a CYP2D6 poor metabolizer genotype or a CYP2D6 poor metabolizer phenotype.

28 Claims, 1 Drawing Sheet

(56) References Cited

U.S. PATENT DOCUMENTS

| | | |
|---|---|---|
| 10,695,304 B2 | 6/2020 | Tabuteau |
| 10,772,850 B2 | 9/2020 | Tabuteau |
| 10,780,064 B2 | 9/2020 | Tabuteau |
| 10,780,066 B2 | 9/2020 | Tabuteau |
| 10,786,469 B2 | 9/2020 | Tabuteau |
| 10,786,496 B2 | 9/2020 | Tabuteau |
| 10,799,497 B2 | 10/2020 | Tabuteau |
| 10,806,710 B2 | 10/2020 | Tabuteau |
| 10,813,924 B2 | 10/2020 | Tabuteau |
| 10,864,209 B2 | 12/2020 | Tabuteau |
| 10,874,663 B2 | 12/2020 | Tabuteau |
| 10,874,664 B2 | 12/2020 | Tabuteau |
| 10,874,665 B2 | 12/2020 | Tabuteau |
| 10,881,624 B2 | 1/2021 | Tabuteau |
| 10,881,657 B2 | 1/2021 | Tabuteau |
| 10,894,046 B2 | 1/2021 | Tabuteau |
| 10,894,047 B2 | 1/2021 | Tabuteau |
| 10,898,453 B2 | 1/2021 | Tabuteau |
| 10,925,842 B2 | 2/2021 | Tabuteau |
| 10,933,034 B2 | 3/2021 | Tabuteau |
| 10,940,124 B2 | 3/2021 | Tabuteau |
| 10,945,973 B2 | 3/2021 | Tabuteau |
| 10,966,941 B2 | 4/2021 | Tabuteau |
| 10,966,942 B2 | 4/2021 | Tabuteau |
| 10,966,974 B2 | 4/2021 | Tabuteau |
| 10,980,800 B2 | 4/2021 | Tabuteau |
| 11,007,189 B2 | 5/2021 | Tabuteau |
| 11,020,389 B2 | 6/2021 | Tabuteau |
| 11,058,648 B2 | 7/2021 | Tabuteau |
| 11,065,248 B2 | 7/2021 | Tabuteau |
| 11,090,300 B2 | 8/2021 | Tabuteau |
| 11,096,937 B2 | 8/2021 | Tabuteau |
| 11,123,343 B2 | 9/2021 | Tabuteau |
| 11,123,344 B2 | 9/2021 | Tabuteau |
| 11,129,826 B2 | 9/2021 | Tabuteau |
| 11,141,388 B2 | 10/2021 | Tabuteau |
| 11,141,416 B2 | 10/2021 | Tabuteau |
| 11,147,808 B2 | 10/2021 | Tabuteau |
| 11,185,515 B2 | 11/2021 | Tabuteau |
| 11,191,739 B2 | 12/2021 | Tabuteau |
| 11,197,839 B2 | 12/2021 | Tabuteau |
| 11,207,281 B2 | 12/2021 | Tabuteau |
| 11,213,521 B2 | 1/2022 | Tabuteau |
| 11,229,640 B2 | 1/2022 | Tabuteau |
| 11,234,946 B2 | 2/2022 | Tabuteau |
| 11,253,491 B2 | 2/2022 | Tabuteau |
| 11,253,492 B2 | 2/2022 | Tabuteau |
| 11,273,133 B2 | 3/2022 | Tabuteau |
| 11,273,134 B2 | 3/2022 | Tabuteau |
| 11,285,118 B2 | 3/2022 | Tabuteau |
| 11,285,146 B2 | 3/2022 | Tabuteau |
| 11,291,638 B2 | 4/2022 | Tabuteau |
| 11,291,665 B2 | 4/2022 | Tabuteau |
| 11,298,351 B2 | 4/2022 | Tabuteau |
| 11,298,352 B2 | 4/2022 | Tabuteau |
| 11,311,534 B2 | 4/2022 | Tabuteau |
| 11,344,544 B2 | 5/2022 | Tabuteau |
| 11,357,744 B2 | 6/2022 | Tabuteau |
| 11,364,233 B2 | 6/2022 | Tabuteau |
| 11,382,874 B2 | 7/2022 | Tabuteau |
| 11,419,867 B2 | 8/2022 | Tabuteau |
| 11,426,370 B2 | 8/2022 | Tabuteau |
| 11,426,401 B2 | 8/2022 | Tabuteau |
| 11,433,067 B2 | 9/2022 | Tabuteau |
| 11,439,636 B1 | 9/2022 | Tabuteau |
| 11,478,468 B2 | 10/2022 | Tabuteau |
| 11,497,721 B2 | 11/2022 | Tabuteau |
| 11,510,918 B2 | 11/2022 | Tabuteau |
| 11,517,542 B2 | 12/2022 | Tabuteau |
| 11,517,543 B2 | 12/2022 | Tabuteau |
| 11,517,544 B2 | 12/2022 | Tabuteau |
| 11,524,007 B2 | 12/2022 | Tabuteau |
| 11,524,008 B2 | 12/2022 | Tabuteau |
| 11,534,414 B2 | 12/2022 | Tabuteau |
| 11,541,021 B2 | 1/2023 | Tabuteau |
| 11,541,048 B2 | 1/2023 | Tabuteau |
| 11,571,399 B2 | 2/2023 | Tabuteau |
| 11,571,417 B2 | 2/2023 | Tabuteau |
| 11,576,877 B2 | 2/2023 | Tabuteau |
| 11,576,909 B2 | 2/2023 | Tabuteau |
| 11,590,124 B2 | 2/2023 | Tabuteau |
| 11,596,627 B2 | 3/2023 | Tabuteau |
| 11,617,728 B2 | 4/2023 | Tabuteau |
| 11,617,747 B2 | 4/2023 | Tabuteau |
| 11,628,149 B2 | 4/2023 | Tabuteau |
| 11,660,273 B2 | 5/2023 | Tabuteau |
| 11,660,274 B2 | 5/2023 | Tabuteau |
| 11,717,518 B1 | 8/2023 | Tabuteau |
| 11,730,706 B1 | 8/2023 | Tabuteau |
| 11,752,144 B1 | 9/2023 | Tabuteau |
| 11,779,579 B2 | 10/2023 | Tabuteau |
| 11,839,612 B1 | 12/2023 | Tabuteau |
| 11,844,797 B1 | 12/2023 | Tabuteau |
| 11,883,373 B1 | 1/2024 | Tabuteau |
| 11,896,563 B2 | 2/2024 | Tabuteau |
| 11,925,636 B2 | 3/2024 | Tabuteau |
| 2002/0035105 A1 | 3/2002 | Caruso |
| 2003/0044462 A1 | 3/2003 | Subramanian et al. |
| 2008/0044462 A1 | 2/2008 | Trumbore et al. |
| 2010/0040679 A1 | 2/2010 | Chang |
| 2010/0291225 A1 | 11/2010 | Fanda et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |
| 2015/0133486 A1 | 5/2015 | Tabuteau |
| 2015/0150830 A1 | 6/2015 | Tabuteau |
| 2015/0157582 A1 | 6/2015 | Tabuteau |
| 2015/0342947 A1 | 12/2015 | Pollard et al. |
| 2016/0008352 A1 | 1/2016 | Tabuteau |
| 2016/0030420 A1 | 2/2016 | Tabuteau |
| 2016/0030421 A1 | 2/2016 | Tabuteau |
| 2016/0128944 A1 | 5/2016 | Chawrai et al. |
| 2016/0128998 A1 | 5/2016 | Tabuteau |
| 2016/0136155 A1 | 5/2016 | Tabuteau |
| 2016/0199321 A1 | 7/2016 | Tabuteau |
| 2016/0228390 A1 | 8/2016 | Tabuteau |
| 2016/0263099 A1 | 9/2016 | Tabuteau |
| 2016/0263100 A1 | 9/2016 | Tabuteau |
| 2016/0317475 A1 | 11/2016 | Tabuteau |
| 2016/0317476 A1 | 11/2016 | Tabuteau |
| 2016/0324807 A1 | 11/2016 | Tabuteau |
| 2016/0339017 A1 | 11/2016 | Tabuteau |
| 2016/0346276 A1 | 12/2016 | Tabuteau |
| 2016/0361305 A1 | 12/2016 | Tabuteau |
| 2016/0375008 A1 | 12/2016 | Tabuteau |
| 2016/0375012 A1 | 12/2016 | Tabuteau |
| 2017/0007558 A1 | 1/2017 | Tabuteau |
| 2017/0014357 A1 | 1/2017 | Tabuteau |
| 2017/0252309 A1 | 9/2017 | Tabuteau |
| 2017/0281617 A1 | 10/2017 | Tabuteau |
| 2017/0304229 A1 | 10/2017 | Tabuteau |
| 2017/0304230 A1 | 10/2017 | Tabuteau |
| 2017/0304298 A1 | 10/2017 | Tabuteau |
| 2017/0354619 A1 | 12/2017 | Tabuteau |
| 2017/0360773 A1 | 12/2017 | Tabuteau |
| 2017/0360774 A1 | 12/2017 | Tabuteau |
| 2017/0360776 A1 | 12/2017 | Tabuteau |
| 2018/0092906 A1 | 4/2018 | Tabuteau |
| 2018/0116980 A1 | 5/2018 | Tabuteau |
| 2018/0133195 A1 | 5/2018 | Tabuteau |
| 2018/0207151 A1 | 7/2018 | Tabuteau |
| 2018/0256518 A1 | 9/2018 | Tabuteau |
| 2018/0360823 A1 | 12/2018 | Tabuteau |
| 2019/0000835 A1 | 1/2019 | Tabuteau |
| 2019/0008800 A1 | 1/2019 | Tabuteau |
| 2019/0008801 A1 | 1/2019 | Tabuteau |
| 2019/0008805 A1 | 1/2019 | Tabuteau |
| 2019/0015407 A1 | 1/2019 | Tabuteau |
| 2019/0083426 A1 | 3/2019 | Tabuteau |
| 2019/0142768 A1 | 5/2019 | Tabuteau |
| 2019/0192450 A1 | 6/2019 | Tabuteau |
| 2019/0192507 A1 | 6/2019 | Tabuteau |

(56) References Cited

U.S. PATENT DOCUMENTS

| | | |
|---|---|---|
| 2019/0216798 A1 | 7/2019 | Tabuteau |
| 2019/0216800 A1 | 7/2019 | Tabuteau |
| 2019/0216801 A1 | 7/2019 | Tabuteau |
| 2019/0290601 A1 | 9/2019 | Tabuteau |
| 2020/0022929 A1 | 1/2020 | Tabuteau |
| 2020/0093762 A1 | 3/2020 | Tabuteau |
| 2020/0147008 A1 | 5/2020 | Tabuteau |
| 2020/0147075 A1 | 5/2020 | Tabuteau |
| 2020/0206217 A1 | 7/2020 | Tabuteau |
| 2020/0215055 A1 | 7/2020 | Tabuteau |
| 2020/0215056 A1 | 7/2020 | Tabuteau |
| 2020/0215057 A1 | 7/2020 | Tabuteau |
| 2020/0215058 A1 | 7/2020 | Tabuteau |
| 2020/0215059 A1 | 7/2020 | Tabuteau |
| 2020/0222389 A1 | 7/2020 | Tabuteau |
| 2020/0230078 A1 | 7/2020 | Tabuteau |
| 2020/0230129 A1 | 7/2020 | Tabuteau |
| 2020/0230130 A1 | 7/2020 | Tabuteau |
| 2020/0230131 A1 | 7/2020 | Tabuteau |
| 2020/0237751 A1 | 7/2020 | Tabuteau |
| 2020/0237752 A1 | 7/2020 | Tabuteau |
| 2020/0246280 A1 | 8/2020 | Tabuteau |
| 2020/0261431 A1 | 8/2020 | Tabuteau |
| 2020/0297666 A1 | 9/2020 | Tabuteau |
| 2020/0338022 A1 | 10/2020 | Tabuteau |
| 2020/0360310 A1 | 11/2020 | Tabuteau |
| 2020/0397723 A1 | 12/2020 | Tabuteau |
| 2020/0397724 A1 | 12/2020 | Tabuteau |
| 2020/0405664 A1 | 12/2020 | Tabuteau |
| 2021/0000763 A1 | 1/2021 | Tabuteau |
| 2021/0000764 A1 | 1/2021 | Tabuteau |
| 2021/0000765 A1 | 1/2021 | Tabuteau |
| 2021/0000768 A1 | 1/2021 | Tabuteau |
| 2021/0000820 A1 | 1/2021 | Tabuteau |
| 2021/0015768 A1* | 1/2021 | Tabuteau ............... A61K 31/15 |
| 2021/0015814 A1 | 1/2021 | Tabuteau |
| 2021/0015815 A1 | 1/2021 | Tabuteau |
| 2021/0023075 A1 | 1/2021 | Tabuteau |
| 2021/0023076 A1 | 1/2021 | Tabuteau |
| 2021/0030747 A1 | 2/2021 | Tabuteau |
| 2021/0030749 A1 | 2/2021 | Tabuteau |
| 2021/0030750 A1 | 2/2021 | Tabuteau |
| 2021/0030751 A1 | 2/2021 | Tabuteau |
| 2021/0046067 A1 | 2/2021 | Tabuteau |
| 2021/0052521 A1 | 2/2021 | Tabuteau |
| 2021/0060004 A1 | 3/2021 | Tabuteau |
| 2021/0060005 A1 | 3/2021 | Tabuteau |
| 2021/0069125 A1 | 3/2021 | Tabuteau |
| 2021/0069128 A1 | 3/2021 | Tabuteau |
| 2021/0077428 A1 | 3/2021 | Tabuteau |
| 2021/0077429 A1 | 3/2021 | Tabuteau |
| 2021/0077483 A1 | 3/2021 | Tabuteau |
| 2021/0106546 A1 | 4/2021 | Tabuteau |
| 2021/0177834 A1 | 6/2021 | Tabuteau |
| 2021/0186899 A1 | 6/2021 | Tabuteau |
| 2021/0186900 A1 | 6/2021 | Tabuteau |
| 2021/0186901 A1 | 6/2021 | Tabuteau |
| 2021/0186955 A1 | 6/2021 | Tabuteau |
| 2021/0186956 A1 | 6/2021 | Tabuteau |
| 2021/0196704 A1 | 7/2021 | Tabuteau |
| 2021/0196705 A1 | 7/2021 | Tabuteau |
| 2021/0205239 A1 | 7/2021 | Tabuteau |
| 2021/0205240 A1 | 7/2021 | Tabuteau |
| 2021/0205297 A1 | 7/2021 | Tabuteau |
| 2021/0220293 A1 | 7/2021 | Tabuteau |
| 2021/0220294 A1 | 7/2021 | Tabuteau |
| 2021/0220348 A1 | 7/2021 | Tabuteau |
| 2021/0260054 A1 | 8/2021 | Tabuteau |
| 2021/0267967 A1 | 9/2021 | Tabuteau |
| 2021/0338605 A1 | 11/2021 | Tabuteau |
| 2021/0346370 A1 | 11/2021 | Tabuteau |
| 2021/0361645 A1 | 11/2021 | Tabuteau |
| 2021/0401828 A1 | 12/2021 | Tabuteau |
| 2021/0401829 A1 | 12/2021 | Tabuteau |
| 2021/0401830 A1 | 12/2021 | Tabuteau |
| 2021/0401831 A1 | 12/2021 | Tabuteau |
| 2022/0008363 A1 | 1/2022 | Tabuteau |
| 2022/0071930 A1 | 3/2022 | Tabuteau |
| 2022/0071931 A1 | 3/2022 | Tabuteau |
| 2022/0079892 A1 | 3/2022 | Tabuteau |
| 2022/0096462 A1 | 3/2022 | Tabuteau |
| 2022/0105086 A1 | 4/2022 | Tabuteau |
| 2022/0133655 A1 | 5/2022 | Tabuteau |
| 2022/0142950 A1 | 5/2022 | Tabuteau |
| 2022/0193012 A1 | 6/2022 | Tabuteau |
| 2022/0218631 A1 | 7/2022 | Tabuteau |
| 2022/0218698 A1 | 7/2022 | Tabuteau |
| 2022/0233470 A1 | 7/2022 | Tabuteau |
| 2022/0233474 A1 | 7/2022 | Tabuteau |
| 2022/0233518 A1 | 7/2022 | Tabuteau |
| 2022/0233519 A1 | 7/2022 | Tabuteau |
| 2022/0241220 A1 | 8/2022 | Tabuteau |
| 2022/0241221 A1 | 8/2022 | Tabuteau |
| 2022/0241269 A1 | 8/2022 | Tabuteau |
| 2022/0241270 A1 | 8/2022 | Tabuteau |
| 2022/0265639 A1 | 8/2022 | Tabuteau |
| 2022/0280504 A1 | 9/2022 | Tabuteau |
| 2022/0313689 A1 | 10/2022 | Tabuteau |
| 2022/0323381 A1 | 10/2022 | Tabuteau |
| 2022/0378779 A1 | 12/2022 | Tabuteau |
| 2023/0045675 A1 | 2/2023 | Tabuteau |
| 2023/0096437 A1 | 3/2023 | Tabuteau |
| 2023/0099206 A1 | 3/2023 | Tabuteau |
| 2023/0100008 A1 | 3/2023 | Tabuteau |
| 2023/0100913 A1 | 3/2023 | Tabuteau |
| 2023/0114111 A1 | 4/2023 | Tabuteau |
| 2023/0131854 A1 | 4/2023 | Tabuteau |
| 2023/0142244 A1 | 5/2023 | Tabuteau |
| 2023/0210843 A1 | 7/2023 | Tabuteau |
| 2023/0218550 A1 | 7/2023 | Tabuteau |
| 2023/0225995 A1 | 7/2023 | Tabuteau |
| 2023/0233491 A1 | 7/2023 | Tabuteau |
| 2023/0241010 A1 | 8/2023 | Tabuteau |
| 2023/0248668 A1 | 8/2023 | Tabuteau |
| 2023/0248669 A1 | 8/2023 | Tabuteau |
| 2023/0255905 A1 | 8/2023 | Tabuteau |
| 2023/0263750 A1 | 8/2023 | Tabuteau |
| 2023/0270740 A1 | 8/2023 | Tabuteau |
| 2023/0277478 A1 | 9/2023 | Tabuteau |
| 2023/0277479 A1 | 9/2023 | Tabuteau |
| 2023/0277480 A1 | 9/2023 | Tabuteau |
| 2023/0277481 A1 | 9/2023 | Tabuteau |
| 2023/0293456 A1 | 9/2023 | Tabuteau |
| 2024/0000770 A1 | 1/2024 | Tabuteau |
| 2024/0016797 A1 | 1/2024 | Tabuteau |
| 2024/0024309 A1 | 1/2024 | Tabuteau |
| 2024/0041862 A1 | 2/2024 | Tabuteau |
| 2024/0041863 A1 | 2/2024 | Tabuteau |
| 2024/0050383 A1 | 2/2024 | Tabuteau |

FOREIGN PATENT DOCUMENTS

| | | |
|---|---|---|
| KR | 101612197 B1 | 4/2016 |
| WO | 1998050044 | 11/1998 |
| WO | 2003086362 A2 | 10/2003 |
| WO | 2004089873 A1 | 10/2004 |
| WO | 2009006194 | 1/2009 |
| WO | 2009050726 A2 | 4/2009 |
| WO | 2015069809 A1 | 5/2015 |
| WO | 2016125108 A1 | 8/2016 |
| WO | 2020146412 A1 | 7/2020 |
| WO | 2021202329 A1 | 10/2021 |
| WO | 2021202419 A1 | 10/2021 |
| WO | 2022119981 A1 | 6/2022 |
| WO | 2023004064 A1 | 1/2023 |

OTHER PUBLICATIONS

Tod et al., Quantitative Prediction of Cytochrome P450 (CYP) 2D6-Mediated Drug Interactions, Clinical Pharmacokinetics, 50(8), 519-530, Aug. 2011.

Kotlyar et al., Inhibition of CYP2D6 Activity by Bupropion, Journal of Clinical Psychopharmacology, 25(2), 226-229, Jun. 2005.

(56) References Cited

OTHER PUBLICATIONS

Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
Auvelity (dextromethorphan hydrobromide and bupropion hydrochloride), Highlights of Prescribing Information and Medication Guide, issued Dec. 2022.
International Preliminary Report on Patentability, PCT/US2021/061492, dated Jun. 15, 2023.
International Search Report and Written Opinion, PCT/US2021/061492 dated Jun. 15, 2023.
International Search Report and Written Opinion, PCT/US2022/012768 dated Jul. 5, 2023.
International Search Report and Written Opinion, PCT/US2023/067062 dated Jul. 12, 2023.
Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.
Anderson, A.; et al. "Efficacy and Safety of AXS-05, an Oral NMDA Receptor Antagonist with Multimodal Activity, in Major Depressive Disorder: Results of a Phase 2, Double-Blind, Active-Controlled Trial" ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).
O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).
O'Gorman, C.; et al. "PMH40 Effects of AXS-05 on Patient Reported Depressive Symptoms in Major Depressive Disorder: Results from the GEMINI Trial" <doi.org/10.1016/j.jval.2021.04.662> (retrieved from internet on Jul. 19, 2023). Value in Health, Jun. 2021, vol. 24, Supplement 1, pp. S135.
O'GORMAN, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.
International Preliminary Report on Patentability, PCT/US2022/012768, dated Jul. 27, 2023.
Nofziger et al., Evaluation of dextromethorphan with select antidepressant therapy for the treatment of depression in the acute care psychiatric setting, Mental Health Clinician, 9(2), 76-81, Mar. 2019.
Update: Bupropion Hydrochloride Extended-Release 300 mg Bioequivalence Studies, FDA, retrieved Mar. 2021.
FDA Draft Guidance on Bupropion Hydrochloride, revised Mar. 2013.
Forfivo XL (bupropion hydrochloride) extended-release tablets, for oral use, Highlights of Prescribing Information, revised Dec. 2019.
Forfivo XL (Bupropion HCl) extended-release tablet, NDA 22497, Jan. 25, 2010.
Wellbutrin XL (bupropion hydrochloride extended-release), Highlights of Prescribing Information, revised Mar. 2022.
Baker T. E. et al., Human Milk and Plasma Pharmacokinetics of Single-Dose Rimegepant 75mg in Healthy Lactating Women, Breastfeeding Medicine, 17(3), 277-282, 2022.
Berle J. O. et al., Antidepressant Use During Breastfeeding, Current Women's Health Reviews, 7(1), 28-34, Feb. 2011.
Briggs G. G. et al., Excretion of bupropion in breast milk, Annals of Pharmacotherapy, 27(4):431-433, Apr. 1993.
Chad L. et al., Update on antidepressant use during breastfeeding, Canadian Family Physician, 59(6), 633-634, Jun. 2013.
Chaudron L. H. et al., Bupropion and Breastfeeding: A case of a possible Infant Seizure, The Journal of clinical psychiatry, 65(6), 881-882, Jun. 2004.
Davis M. F. et al., Bupropion Levels in Breast Milk for 4 Mother-Infant Pairs: More Answers to Lingering Questions, J. Clin. Psychiatry, 70(2), 297-298, Feb. 2009.
Di Scalea T. L. et al., Antidepressant Medication Use during Breastfeeding, Clinical obstetrics and gynecology, 52(3): 483-497, Sep. 2009.
Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.
Gentile S, The safety of newer antidepressants in pregnancy and breastfeeding, Drug Safety, 28(2), 137-152, Feb. 2005. [doi: 10.2165/00002018-200528020-00005. PMID: 15691224.].
Haas J. S. et al., Bupropion in breast milk: an exposure assessment for potential treatment to prevent post-partum tobacco use, Tobacco Control, 13(1), 52-56, Mar. 2004.
Ram D. et al., Antidepressants, anxiolytics, and hypnotics in pregnancy and lactation, Indian J Psychiatry, 57(Suppl 2): S354-S371, Jul. 2015. [doi:10.4103/0019-5545.161504].
Weissman A. M. et al., Pooled Analysis of Antidepressant Levels in Lactating Mothers, Breast Milk, and Nursing Infants, Am J Psychiatry, 161(6), 1066-1078, Jun. 2004.
Horn J. R. et al., Get to Know an Enzyme: CYP2D6, Pharmacy Times, Jul. 2008, retrieved on Aug. 28, 2023.
International Search Report and Written Opinion, PCT/US2023/069286 dated Aug. 22, 2023.
International Search Report and Written Opinion, PCT/US2023/069239 dated Aug. 28, 2023.
International Search Report and Written Opinion, PCT/US2023/069367 dated Aug. 28, 2023.
International Search Report and Written Opinion, PCT/US2023/069655 dated Sep. 15, 2023.
International Search Report and Written Opinion, PCT/US2023/069371 dated Sep. 26, 2023.
International Search Report and Written Opinion, PCT/US2022/037913 mailed on Sep. 21, 2022.
Jones A et al., "Early Improvements in Functioning and Quality of Life With AXS-05 in Major Depressive Disorder: Results From the Gemini Trial ," Value in Health, Jun. 2021, vol. 24, abstract No. PHM42, page S135. DOI: 10.1016/j.jval.2021.04.662.
International Search Report and Written Opinion, PCT/US2022/074713 mailed on Sep. 21, 2022.
Axsome Therapeutics, Inc.: "Merit: A Randomized, Double-blind, Placebo-controlled Study of AXS-05 for Relapse Prevention in Treatment Resistant Depression," ClinicalTrials.gov, NCT04608396 version 2, Mar. 24, 2021.
International Preliminary Report on Patentability, PCT/US2022/037913, issued on Jan. 18, 2024.
International Preliminary Report on Patentability, PCT/US2022/074713, issued on Feb. 22, 2024.
Chinese Pat. No. 202080004041.1 Invalidation Notice and Request issued on Jan. 15, 2024. (English translation included).

\* cited by examiner

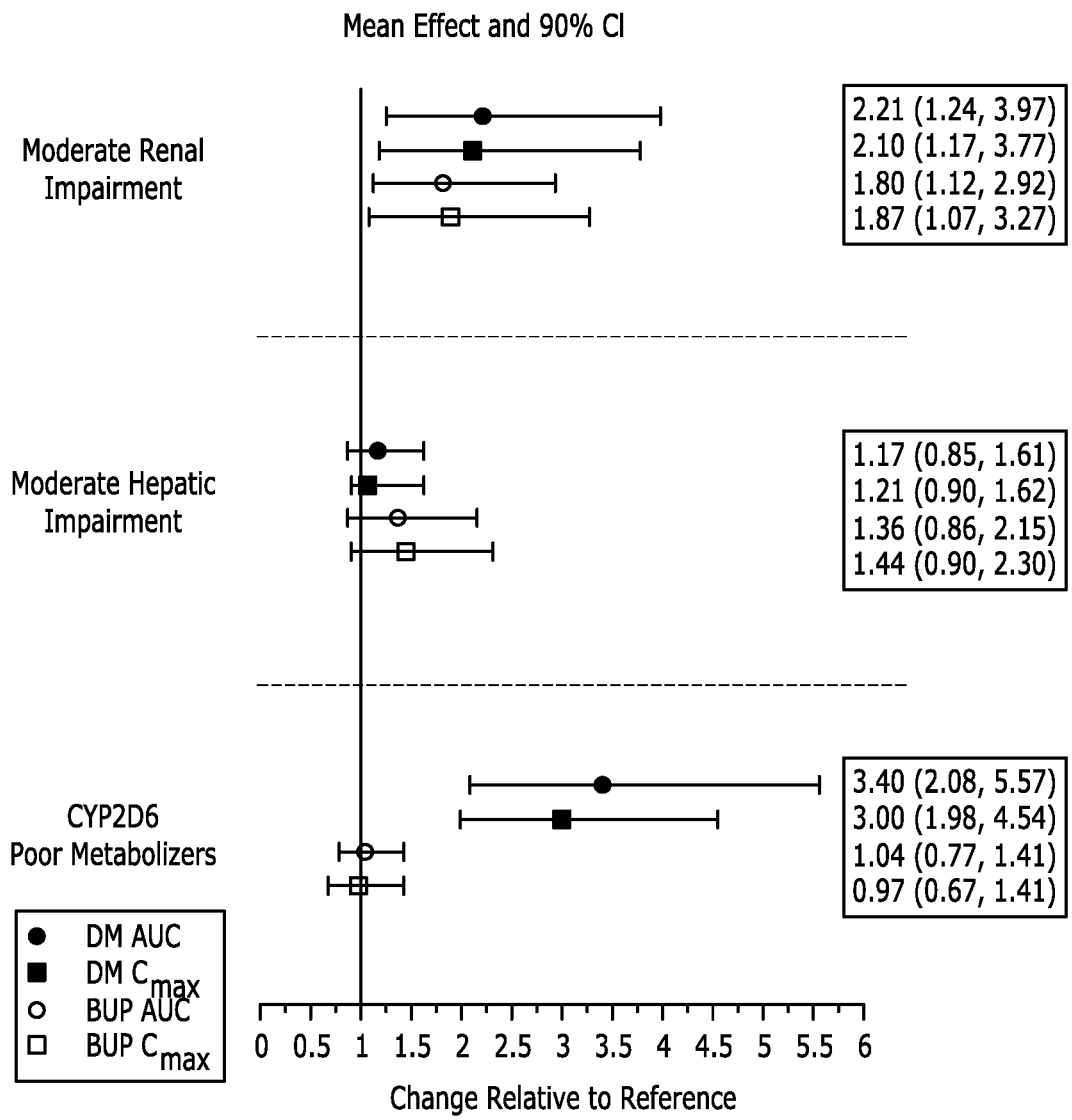

TREATMENT OF POOR METABOLIZERS OF DEXTROMETHORPHAN WITH A COMBINATION OF BUPROPION AND DEXTROMETHORPHAN

CROSS REFERENCE TO RELATED APPLICATIONS

This application is a continuation of U.S. patent application Ser. No. 18/169,571, filed Feb. 15, 2023; which claims benefit of U.S. Provisional App. Nos. 63/357,471, filed Jun. 30, 2022, 63/370,577, filed Aug. 5, 2022; 63/370,769, filed Aug. 8, 2022; all of which are incorporated by reference in their entireties.

FIELD

This disclosure relates to treatment of various neurological and psychiatric disorders or conditions with a combination of bupropion and dextromethorphan in patients who have a CYP2D6 poor metabolizer genotype or a CYP2D6 poor metabolizer phenotype.

SUMMARY

Disclosed herein is a method of treating a nervous system condition (such as depression, e.g., major depressive disorder, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) in a CYP2D6 poor metabolizer comprising administering a daily dose of 105 mg of bupropion hydrochloride and 45 mg of dextromethorphan hydrobromide, such as in a once daily dose, to a human patient in need thereof, wherein the human patient is known to be a poor CYP2D6 metabolizer.

Disclosed herein is a method of safely treating a patient having major depressive disorder by administering a combination of dextromethorphan and bupropion. This method is intended for patients having a neurological disorder or condition or a psychiatric disorder or condition, such as major depressive disorder, and a CYP2D6 poor metabolizer genotype or a CYP2D6 poor metabolizer phenotype. Typically, the CYP2D6 genotype or phenotype is determined by performing an assay on a biological sample from the patient. In this method a dosage form is orally administered, for example, once a day to a patient. The dosage form comprises a combination of 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of bupropion to dextromethorphan in the dosage form is about the ratio of the molar amount of bupropion in 105 mg of bupropion hydrochloride to the molar amount of dextromethorphan in 45 mg of dextromethorphan hydrobromide. Alternatively, a dose of about 52.5 mg or less of bupropion hydrochloride, or a molar equivalent amount of the free base form or another salt form of bupropion, and 22.5 mg or less of dextromethorphan hydrobromide, or a molar equivalent amount of the free base form or another salt form of dextromethorphan may be orally administered twice a day. As a result, a risk of dizziness, a potential side effect of dextromethorphan exposure, for a patient having a CYP2D6 poor metabolizer genotype is lower following orally administering the dosage form containing the combination once a day to the patient than it would be if a combination of 105 mg or of bupropion hydrochloride and 45 mg of dextromethorphan hydrobromide were administered twice a day to the patient for the same number of days.

In some embodiments, if the patient does not have a CYP2D6 poor metabolizer genotype or a CYP2D6 poor metabolizer phenotype, then a dosage form is orally administering twice a day to the patient, Wherein the dosage form contains a combination of 105 mg or more of bupropion hydrochloride, or a molar equivalent amount of the free base or another salt form of bupropion, and 45 mg or more of dextromethorphan hydrobromide, or a molar equivalent amount of the free base or another salt form of dextromethorphan.

BRIEF DESCRIPTION OF THE DRAWINGS

FIG. 1 depicts the effects of renal impairment, hepatic impairment, and CYP2D6 poor metabolizer status on the pharmacokinetics of a tablet containing 45 mg of dextromethorphan hydrobromide and 105 mg of bupropion hydrochloride.

DETAILED DESCRIPTION

Disclosed herein is a method of treating a nervous system condition (such as depression, e.g., major depressive disorder, agitation associated with Alzheimer's disease (or agitation associated with dementia of the Alzheimer's type), agitation associated with dementia, anxiety (or generalized anxiety disorder), neuropathic pain, or peripheral diabetic neuropathic pain) in a CYP2D6 poor metabolizer comprising administering a daily dose of 105 mg of bupropion hydrochloride and 45 mg of dextromethorphan hydrobromide, such as in a once daily dose, to a human patient in need thereof, wherein the human patient is known to be a poor CYP2D6 metabolizer.

In some embodiments, the combination of 105 mg of bupropion hydrochloride and 45 mg of dextromethorphan hydrobromide is present in a tablet.

In some embodiments, the once-daily administration avoids the human patient having an about 3.4-fold increase in $AUC_{0\text{-}12}$ of dextromethorphan as compared to the $AUC_{0\text{-}12}$ of dextromethorphan that would result after 8 days of twice daily administration of the tablet to a human patient who is an extensive or ultra-extensive CYP2D6 metabolizer.

In some embodiments, the once-daily administration avoids the patient having about 3-fold increase in $C_{max}$ of dextromethorphan as compared to the $C_{max}$ of dextromethorphan that would result after 8 days of twice daily administration of the tablet to a human patient who is an extensive or ultra-extensive CYP2D6 metabolizer.

In some embodiments, the tablet is orally administered in the morning.

In some embodiments, the dextromethorphan is in an immediate-release formulation.

In some embodiments, the bupropion is in an extended-release formulation.

In some embodiments, the tablet further contains a carbomer homopolymer.

In some embodiments, the tablet further contains colloidal silicon dioxide.

In some embodiments, the tablet further contains crospovidone.

In some embodiments, the tablet further contains glyceryl monocaprylocaprate.

In some embodiments, the tablet further contains L-cysteine hydrochloride monohydrate.

In some embodiments, the tablet further contains magnesium stearate.

In some embodiments, the tablet further contains microcrystalline cellulose.

In some embodiments, the tablet further contains polyvinyl alcohol.

In some embodiments, the tablet further contains red iron oxide.

In some embodiments, the tablet further contains sodium lauryl sulfate.

In some embodiments, the tablet further contains stearic acid.

In some embodiments, the tablet further contains talc.

In some embodiments, the tablet further contains titanium dioxide.

In some embodiments, the tablet further contains yellow iron oxide.

In some embodiments, the twice-daily administration of the tablet to the human patient for 8 days would result in the human patient having about same $AUC_{0-12}$ of bupropion as compared to the $AUC_{0-12}$ of bupropion that would result after 8 days of twice daily administration of the tablet to a human patient who is an extensive or ultra-extensive CYP2D6 metabolizer.

In some embodiments, the twice-daily administration of the tablet to the human patient for 8 days would result in the human patient having about same $C_{max}$ of bupropion as compared to the $C_{max}$ of bupropion that would result after 8 days of twice daily administration of the tablet to a human patient who is an extensive or ultra-extensive CYP2D6 metabolizer.

The chemical name of dextromethorphan hydrobromide is morphinan, 3-methoxy-17-methyl-, (9α, 13α, 14α), hydrobromide monohydrate. Dextromethorphan hydrobromide has the empirical formula $C_{18}H_{25}NO \cdot HBr \cdot H_2O$ and a molecular weight of 370.33 (271.4 dextromethorphan base). The structural formula is:

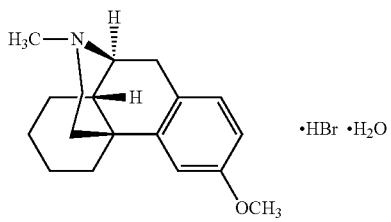 [SMILES: COc1ccc2c(c1)[C@]13CCCC[C@@H]1[C@H](C2)N(C)CC3 ; Br ; O]

Dextromethorphan hydrobromide powder is white or almost white, crystalline, and sparingly soluble in water.

The chemical name of bupropion hydrochloride is: (±)-1-(3-chlorophenyl)-2-[(1,1-dimethylethyl)amino]-1-propanone hydrochloride. Bupropion hydrochloride has the empirical formula $C_{13}H_{18}ClNO \cdot HCl$ and a molecular weight of 276.2 (239.74 bupropion base). The structural formula is:

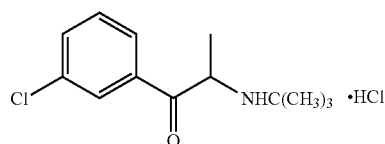

Bupropion hydrochloride powder is white and highly soluble in water.

Cytochrome P450 2D6 (CYP2D6) is an enzyme that in humans is encoded by the CYP2D6 gene. The CYP2D6 function in any particular subject may be described as one of the following: 1) a poor metabolizer, who has little or no CYP2D6 function; 2) an extensive metabolizer, who has normal CYP2D6 function; 3) an intermediate metabolizer, who metabolizes drugs at a rate somewhere between the poor and extensive metabolizers; and 4) an ultrarapid metabolizer, who has multiple copies of the CYP2D6 gene that are expressed, so that greater-than-normal CYP2D6 function occurs. See, e.g., Bertilsson et al. Molecular genetics of CYP2D6: clinical relevance with focus on psychotropic drugs, British Journal of Clinical Pharmacology, 53(2): 111-22, February 2002. Patients who do not have a CYP2D6 poor metabolizer genotype or a CYP2D6 poor metabolizer phenotype, include intermediate metabolizers, extensive metabolizers, or ultrarapid metabolizers.

This disclosure relates to treating patients with a CYP2D6 poor metabolizer genotype or a CYP2D6 poor metabolizer phenotype. Individuals with a CYP2D6 poor metabolizer genotype may be identified by obtaining a biological sample, such as a blood sample, a saliva sample, or any other sample containing the individual's DNA, and performing a genotyping assay. A CYP2D6 poor metabolizer phenotype may be obtained by comparing the plasma levels of dextromethorphan of a patient from administering dextromethorphan alone to those that would be expected based upon the dose of a combination of bupropion and dextromethorphan administered to the patient. It may also be determined by administering dextromethorphan alone and comparing the dextromethorphan/dextrorphan metabolic ratio in a patient, e.g., as described in Jurica et al. Journal of Clinical Pharmacology and Therapeutics, 2012, 37, 486-490. Typically, a metabolic ratio of dextromethorphan/dextrorphan of 0.3 or greater indicates a poor metabolizer phenotype.

There are many other genotyping tests that may be used to determine whether a person is a poor CYP2D6 metabolizer. See, e.g. Schaeffeler et al. CYP2D6 Genotyping Strategy Based on Gene Copy Number Determination by TaqMan Real-Time PCR. Human Mutation 22, 476-485 (2003); Bradford L D. CYP2D6 allele frequency in European Caucasians, Asians, Africans, and their descendants. Pharmacogenomics 2002 March; 3(2):229-43; Bertilsson L, Dahl M L, Dalen P, Al-Shurbaji A. Molecular genetics of CYP2D6: clinical relevance with focus on psychotropic drugs. Br J Clin Pharmacol 2002 February; 53(2): 111-22; Bryan Campbell, Pharm. D., Jane Xu, Ph.D., Josephine Cucchiaro, Ph.D., Mila Etropolski, M. D., Mark Schmidt, M. D. Protocol No. CILO522A2328. 22 Oct. 2001. Chainvuati S, Nafziger A N, Leeder J S, Gaedigk A, Kearns G L, Sellers E, Zhang Y, Kashuba A D, Rowland E, Bertino J S Jr. Combined phenotypic assessment of cytochrome p450 1A2, 2C9, 2C19, 2D6, and 3A, N-acetyltransferase-2, and xanthine oxidase activities with the "Cooperstown 5+1 cocktail." Clin. Pharmacol. Ther. 2003 November; 74(5): 437-47; Dahl M L, Yue Q Y, Roh H K, Johansson I, Sawe J, Sjoqvist F, Bertilsson L. Genetic analysis of the CYP2D locus in relation to debrisoquine hydroxylation capacity in Korean, Japanese and Chinese subjects. Pharmacogenetics 1995 June; 5(3):159-64; Gough A C, Miles J S, Spurr N K, Moss J E, Gaedigk A, Eichelbaum M, Wolf C R. Identification of the primary gene defect at the cytochrome P450 CYP2D locus. Nature 1990 Oct. 5; 47(6295):773-6; Hanioka N, Kimura S, Meyer U A, Gonzalez F J. The human CYP2D locus associated with a common genetic defect in drug oxidation: a G1934—A base change in intron 3 of a mutant CYP2D6 allele results in an aberrant 3' splice recognition site. Am J Hum Genet. 1990 December; 47(6): 994-1001; Jaanson P, Marandi T, Kiivet R A, Vasar V, Vaan S, Svensson J O, Dahl M L. Maintenance therapy with zuclopenthixol decanoate: associations between plasma concentrations, neurological side effects and CYP2D6 genotype. Psychopharmacology (Berl) 2002 June; 162(1):67-73; Johansson I, Oscarson M, Yue Q Y, Bertilsson L, Sjoqvist F, Ingelman-Sundberg M. Genetic analysis of the Chinese cytochrome P4502D locus: characterization of variant CYP2D6 genes present in subjects with diminished capacity for debrisoquine hydroxylation: Mol Pharmacol 1994 September; 46(3):452-9; Juif Jen, Sujata Vaidyanathan, Michael Hayes. Clinical Pharmacology Report: Protocol No CILO522A 2328: 12 Jul. 2002; Kagimoto M, Heim M, Kagimoto K, Zeugin T, Meyer U A. Multiple mutations of the human cytochrome P450IID6 gene (CYP2D6) in poor metabolizers of debrisoquine. Study of the functional significance of individual mutations by expression of chimeric genes. J Biol Chem 1990 Oct. 5; 265(28):17209-14; Lyamichev V, Mast A L, Hall J G, Prudent J R, Kaiser M W, Takova T, Kwiatkowski R W, Sander T J, de Arruda M, Arco D A, Neri B P, Brow M A. Polymorphism identification and quantitative detection of genomic DNA by invasive cleavage of oligonucleotide probes. Nat Biotechnol 1999 March; 17(3):292-6; McElroy S, Richmond J, Lira M, Friedman D, Silber B M, Milos P M, Sachse C, Brochmoller, Roots I. CYP2D6 genotyping as an alternative to phenotyping for determination of metabolic status in a clinical trial setting. AAPS Pharmsci 2000; 2(4):article 33; Nevilie M, Selzer R, Aizenstein B, Maguire M, Hogan K, Walton R, Welsh K, Neri B, de Arruda M. Characterization of cytochrome P450 2D6 alleles using the Invader system. Biotechniques 2002 June; Suppl:34-8, 40-3; and Yokota H, Tamura S, Furuya H, Kimura S, Watanabe M, Kanazawa I, Kondo I, Gonzalez F J. Evidence for a new variant CYP2D6 allele CYP2D6) in a Japanese population associated with lower in vivo rates of sparteine metabolism: Pharmacogenetics 1993 October; 3(5):256-63.

In some embodiments, the patient has a CYP2D6G1846 (AA) genotype. In some embodiments, the patient has a CYP2D6G1846 (AG) genotype. In some embodiments, the patient has a CYP2D6C100T (TT) genotype. In some embodiments, the patient has a CYP2D6C100T (CT) genotype.

Patients having a CYP2D6 poor metabolizer genotype or a CYP2D6 poor metabolizer phenotype may be treated for a neurological disorder or condition or a psychiatric disorder or condition by orally administering once a day to the patient, a dosage form containing a combination of 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of bupropion to dextromethorphan is about the ratio of the molar amount of bupropion in 105 mg of bupropion hydrochloride to the molar amount of dextromethorphan in 45 mg of dextromethorphan hydrobromide. Alternatively, a dose of about 52.5 mg or less of bupropion hydrochloride, or a molar equivalent amount of the free base form or another salt form of bupropion, and 22.5 mg or less of dextromethorphan hydrobromide, or a molar equivalent amount of the free base form or another salt form of dextromethorphan may be administered twice a day.

Administering bupropion in combination with dextromethorphan to a human being having a CYP2D6 poor metabolizer genotype or a CYP2D6 poor metabolizer phenotype has been found to result in higher blood plasma levels of dextromethorphan as compared to a patient who does not have a poor metabolizer genotype or phenotype. This raises safety concerns for the poor metabolizers because of the increased risk of adverse events associated with high blood plasma levels of dextromethorphan.

For some patients, potential adverse events from increased dextromethorphan exposure may include dizziness, nausea, dry mouth, somnolence, headache, agitation, hypomania, confusion, including mental confusion, hallucinations, coma, drowsiness shivering, hyperthermia, vasoconstriction, tachycardia, diarrhea, myoclonus (muscle twitching), hyperreflexia (manifested by clonus), tremor, restlessness, insomnia, dissociation, vomiting, delusions of grandeur, blurred vision, double vision, bloodshot eyes, dilated pupils, sweating, fever, bruxia (teeth grinding), hypotension, hypertension, shallow respiration, slowed breathing, difficulty in urination, urinary retention, muscle spasms, shakiness, sedation, paresthesia, hypomania, slurred speech, unsteady walk, blackouts, inability to focus eyes, skin rash, severe itchiness, spontaneous memory recall, acute psychosis, unusual excitement, nervousness, irritability, constipation, stomach pain, etc. Administering a lower dose, such as half the dose or less, may decrease the risk of any of these adverse events. For example, the dosage form may be administered once a day instead of twice a day. Alternatively, or additionally, the amount of bupropion and dextromethorphan may be reduced. For example, the amount of bupropion and dextromethorphan may be reduced by 50%, 75%, 90%, or more. Administering the reduced and/or less frequent dose of bupropion and dextromethorphan (for example administering a combination of 105 mg of bupropion hydrochloride and 45 mg of dextromethorphan hydrobromide once a day) may have a reduced risk of the adverse event as compared to administering a combination of 105 mg of bupropion hydrochloride and 45 mg of dextromethorphan hydrobromide twice a day to the patient.

A dosage form described herein may include, or be prepared from, any suitable form of bupropion, such as a salt form, e.g., bupropion hydrochloride, other salt forms, the free base form, hydrates, solvates, polymorphs, other solid forms, etc. In some embodiments, the pharmaceutical composition is free of any other active pharmaceutical agents other than a bupropion and/or a dextromethorphan.

The dosage form for administering to a patient who has a CYP2D6 poor metabolizer genotype or a CYP2D6 poor metabolizer phenotype may include any suitable amount of bupropion for once daily administration, i.e. less than 105 mg, such as about 1-105 mg, about 1-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-105 mg, about 103-107 mg, about 105 mg, about 53 mg, about 26 mg, about 13 mg, or about 12 mg of bupropion hydrochloride, a molar equivalent amount of another salt form of bupropion, or the free base form of bupropion.

Alternatively, the dosage form for administering to a patient who has a CYP2D6 poor metabolizer genotype or a CYP2D6 poor metabolizer phenotype may be administered twice a day, and that daily dose may be less than 105 mg, such as about 1-105 mg, about 1-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-105 mg, about 103-107 mg, about 105 mg, about 53 mg, about 26 mg, about 13 mg, or about 12 mg of bupropion hydrochloride, a molar equivalent amount of another salt form of bupropion, or the free base form of bupropion.

In some embodiments, the dosage form provides sustained release of bupropion.

A dosage form described herein may include, or be prepared from, any suitable form of dextromethorphan, such as a salt form, e.g., dextromethorphan bromide, other salt forms, the free base form, hydrates, solvates, polymorphs, other solid forms, etc.

The dosage form for administering to a patient who has a CYP2D6 poor metabolizer genotype or a CYP2D6 poor metabolizer phenotype may include any suitable amount of dextromethorphan for once daily administration, i.e. less than 45 mg, such as about 1-45 mg, about 1-5 mg, about 5-10 mg, about 10-20 mg, about 20-30 mg, about 30-40 mg, about 40-45 mg, about 45 mg, about 34 mg, about 23 mg, about 11 mg, about 6 mg, or about 5 mg of the dextromethorphan, such as dextromethorphan bromide, a molar equivalent amount of another salt form of dextromethorphan, or the free base form of dextromethorphan.

Alternatively, the dosage form for administering to a patient who has a CYP2D6 poor metabolizer genotype or a CYP2D6 poor metabolizer phenotype may be administered twice a day, and that daily dose may be, for example, about 1-45 mg, about 1-5 mg, about 5-10 mg, about 10-20 mg, about 20-30 mg, about 30-40 mg, about 40-45 mg, about 45 mg, about 34 mg, about 23 mg, about 11 mg, about 6 mg, or about 5 mg of the dextromethorphan, such as dextromethorphan bromide, a molar equivalent amount of another salt form of dextromethorphan, or the free base form of dextromethorphan.

In some embodiments, the dosage form provides immediate release of dextromethorphan.

The pharmaceutical dosage form has a molar ratio of bupropion to dextromethorphan in the dosage form that is about the ratio of the molar amount of bupropion in 105 mg of bupropion hydrochloride to the molar amount of dextromethorphan in 45 mg of dextromethorphan hydrobromide. There are 0.38 moles of bupropion in 105 mg of bupropion hydrochloride (Molecular weight: 276.2 g/mol); and there are 0.122 moles of dextromethorphan in 45 mg of dextromethorphan hydrobromide (Molecular weight: 370.3 g/mol). So, this ratio is about 0.38 moles of bupropion to about 0.12 mole of dextromethorphan. In some embodiments, the ratio is about 0.37-0.39 moles of bupropion to about 0.11-0.13 moles of dextromethorphan, about 2.5-3.1 to 1, about 2.6-3.3 to 1, or about 2.5-3.3 to 1.

Pope reported that when CYP2D6 was inhibited by administering quinidine, the $C_{max}$ of dextromethorphan was about 40% higher for poor metabolizers and the $AUC_{0-12}$ of dextromethorphan was about 46% higher for CYP2D6 poor metabolizers, as compared to other patients who were not CYP2D6 poor metabolizers. (Pope, et al., J. Clin Pharmacol 2004; 44:1132-1142.) Bupropion also is a CYP2D6 inhibitor. The inventor has found that, like quinidine, administration of the combination of bupropion and dextromethorphan results in poor metabolizers having a significantly higher $C_{max}$ and AUC of dextromethorphan than other patients who are not poor metabolizers (e.g., extensive, intermediate, or ultra-rapid metabolizers).

When the combination of bupropion and dextromethorphan is administered to CYP2D6 poor metabolizers, there would be no particular reason to believe that the $C_{max}$ and AUC of bupropion would be different than that of other patients who are not poor metabolizers (e.g., extensive, intermediate, or ultra-rapid metabolizers). Thus, a person of ordinary skill in the art would expect that, when the combination of bupropion and dextromethorphan is administered to CYP2D6 poor metabolizers, the CYP2D6 poor metabolizers would have blood plasma levels of bupropion that are similar to other patients who are not poor metabolizers (e.g., extensive, intermediate, or ultra-rapid metabolizers), but would have significantly higher blood plasma levels of dextromethorphan. The inventor has found this to be the case in clinical trials. This increase in dextromethorphan exposure for CYP2D6 poor metabolizers increases the risk of adverse events caused by dextromethorphan as compared to patients who do not have a CYP2D6 poor metabolizer genotype or a CYP2D6 poor metabolizer phenotype.

The antidepressive efficacy of bupropion has been shown to be dose dependent. (See https://dailymed.nlm.nih.gov/dailymed/lookup.cfm?setid=a0fdfc21-165a-43fa-9 b3c-e4813 b892250&version=3.) Thus, reducing the dose of bupropion would be expected to result in a loss in the antidepressive effect of bupropion, especially when the dose (e.g., 210 mg/day) is already below the target dose of bupropion for treating depression. To avoid losing efficacy of bupropion, a person of ordinary skill in the art would likely decrease the dose of dextromethorphan while keeping the same dose of bupropion. For example, a person of ordinary skill in the art might reduce the dextromethorphan dose from 90 mg/day to 45 mg/day while maintaining a 210 mg/day dose of bupropion. This would be expected to result in CYP2D6 poor metabolizer having similar plasma levels of both bupropion and dextromethorphan as the plasma levels of bupropion and dextromethorphan in other patients who are not CYP2D6 poor metabolizer (e.g., extensive, intermediate, or ultra-rapid metabolizers).

However, the inventor believes that the dose of both bupropion and dextromethorphan can be reduced by the same proportion (e.g. by giving a dosage form containing 105 mg of bupropion hydrochloride and 45 mg of dextromethorphan once a day instead of giving a dosage form with 105 mg of bupropion hydrochloride and 45 mg of dextromethorphan twice a day or giving a dosage form with 210 mg of bupropion hydrochloride and 90 mg of dextromethorphan once a day) without reducing the therapeutic effect of the combination in the treatment of depression.

In some embodiments, the dosage form may contain bupropion and dextromethorphan, and no other active pharmaceutical ingredients. In some embodiments, the bupropion and the dextromethorphan are in two different layers or phases of the dosage form, e.g., each layer contains only bupropion or dextromethorphan and none of the other.

The pharmaceutical composition or dosage form may include cysteine (e.g., L-cysteine), such as about 30-100 mg, or about 50-100 mg of the cysteine, such as L-cysteine hydrochloride, another salt form of L-cysteine, or the neutral or zwitterionic form of L-cysteine. Cysteine in these amounts may be helpful in stabilizing bupropion in the presence of other excipients.

The pharmaceutical composition or dosage form may further comprise a sustained release or controlled release polymer, e.g., a polymer for providing sustained release of bupropion, such as a crosslinked or uncross linked acrylate polymer or copolymer (including a poly(acrylic acid) or a poly(alkacrylic acid), such as poly(methacrylic acid), e.g., a carbomer homopolymer Type A such as Carbopol 971P), a cellulose derivative, such as methylcellulose, etc. In some embodiments, the controlled release polymer (e.g., a carbomer copolymer Type A) is about 1-40%, about 1-5%, about 5-10%, about 10-15%, about 15-20%, about 20-30%, about 30-40%, about 11-13%, or about 12% of the weight of the pharmaceutical composition. In some embodiments, the controlled release polymer is about 0.1-20%, about 0.1-2%, about 2-4%, about 4-6%, about 6-8%, about 8-10%, about 10-15%, about 15-20%, or about 7% of the weight of the dosage form.

The pharmaceutical composition or dosage form may further comprise a filler such as microcrystalline cellulose. In some embodiments, the filler may be about 20-60%, about 20-30%, about 30-40%, about 40-50%, or about 50-60% of the weight of the pharmaceutical composition or the dosage form.

The pharmaceutical composition or dosage form may further comprise a lubricant such as magnesium stearate. In some embodiments, the lubricant is about 0.1-10%, about 0.1-2%, about 2-4%, about 4-6%, about 6-8%, or about 8-10% of the weight of the pharmaceutical composition or the dosage form.

The dosage form may be formulated for any suitable route of administration, such as oral administration.

Dosage forms, such as solid dosage forms, e.g., capsules, tablets, or pills, for oral administration may also contain one or more of the following: a binder such as gum tragacanth, acacia, corn starch, or gelatin; an excipient, such as dicalcium phosphate; a disintegrating agent such as corn starch, potato starch, alginic acid, and the like; a sweetening agent such as sucrose, lactose, or saccharin; or a flavoring agent such as peppermint, oil of wintergreen, or cherry flavoring. When the dosage form is a capsule, it may contain, in addition to materials of the above type, a liquid carrier. Various other materials may be present as a coating, for example, tablets, pills, or capsules may be coated with shellac, sugar, or both. It may be desirable for material in a dosage form or pharmaceutical composition to be pharmaceutically pure and nontoxic in the amounts employed. In some embodiments, the dosage form contains cysteine, Carbopol 971P, microcrystalline cellulose, silicon dioxide, and magnesium. In some embodiments, the dosage form contains a first layer comprising bupropion and cysteine, and a second layer comprising dextromethorphan, microcrystalline cellulose, croscarmellose sodium, and magnesium stearate.

An example of a bilayer dosage form is shown below:

| Layer 1 | |
|---|---|
| Ingredient | Amount (mg) |
| Bupropion Hydrochloride | 105 |
| Cysteine | 10-100 |
| Carbopol 971P | 20-60 |
| Microcrystalline Cellulose | 200-300 |
| Colloidal Silicon Dioxide | 1-10 |
| Magnesium Stearate | 1-10 |

| Layer 2 | |
|---|---|
| Ingredient | Amount (mg) |
| Dextromethorphan hydrobromide | 45 |
| Microcrystalline Cellulose | 100-150 |
| Croscarmellose sodium | 1-20 |
| Magnesium Stearate | 1-10 |

The pharmaceutical compositions or dosage forms described herein may be useful in treating neurological disorders or psychiatric conditions, such as depression, including major depressive disorder or treatment-resistant major depressive disorder, agitation, such as agitation associated with Alzheimer's disease, addiction, such as nicotine addiction, etc., in genotypically poor metabolizers of dextromethorphan. For example, the pharmaceutical composition or dosage form may be administered once a day to a human being suffering from a neurological disorder or psychiatric condition. Treatment may be continued as needed while the treatment is effective and safe, e.g., for at least 1 week, at least 2 weeks, at least 4 weeks, at least one month, at least 2 months, at least 3 months, at least 6 months, at least 1 year, 1 week to 2 months, 1-3 months, 3-6 months, 6-12 months, 1-2 years, or possibly longer.

The CYP2D6 gene is highly polymorphic, with more than 70 allelic variants described so far. See, e.g., http://www.imm.ki.se/CYPalleles/cyp2d6.htm. Two common polymorphisms within the CYP2D6 gene in Caucasian populations are CYP2D6G1846A and CYP2D6P34S (also referred to as CYP2D6C100T). These polymorphisms correspond to nucleotides 3465 and 1719, respectively, in GenBank sequence M33388.1 (GI:181303). The CYP2D6P34S/CYP2D6C100T polymorphism also corresponds to nucleotide 100 in GenBank mRNA sequence M20403.1 (GI:181349).

The CYP2D6G1846A polymorphism (known as the CYP2D6*4 alleles, encompassing *4A, *4B, *4C, *4D, *4E, *4F, *4G, *4H, *4J, *4K, and *4L) represents a G to A transition at the junction between intron 3 and exon 4, shifting the splice junction by one base pair, resulting in frameshift and premature termination of the protein (Kagimoto M, Heim M, Kagimoto K, Zeugin T, Meyer U A. Multiple mutations of the human cytochrome P450IID6 gene (CYP2D6) in poor metabolizers of debrisoquine. Study of the functional significance of individual mutations by expression of chimeric genes. J Biol Chem 1990 Oct. 5; 265(28):17209-14; Gough A C, Miles J S, Spurr N K, Moss J E, Gaedigk A, Eichelbaum M, Wolf C R. Identification of the primary gene defect at the cytochrome P450 CYP2D locus. Nature 1990 Oct. 5; 47(6295):773-6; Hanioka N, Kimura S, Meyer U A, Gonzalez F J. The human CYP2D locus associated with a common genetic defect in drug oxidation: a G1934—A base change in intron 3 of a mutant CYP2D6 allele results in an aberrant 3' splice recognition site. Am J Hum Genet. 1990 December; 47(6):994-1001). The CYP2D6P34S/CYP2D6C100T polymorphism (known as the CYP2D6*10 and CYP2D6*14 alleles) represents a C to T change that results in the substitution of a Proline at position 34 by Serine (Yokota H, Tamura S, Furuya H, Kimura S, Watanabe M, Kanazawa I, Kondo I, Gonzalez F J. Evidence for a new variant CYP2D6 allele CYP2D6) in a Japanese population associated with lower in vivo rates of sparteine metabolism: Pharmacogenetics 1993 October; 3(5):256-63; Johansson I, Oscarson M, Yue Q Y, Bertilsson L, Sjoqvist F, Ingelman-Sundberg M. Genetic analysis of the Chinese cytochrome P4502D locus: characterization of variant CYP2D6 genes present in subjects with diminished capacity for debrisoquine hydroxylation: Mol Pharmacol 1994 September; 46(3):452-9). Both of these polymorphisms have been associated with reduced enzymatic activity for different substrates (Johansson I, Oscarson M, Yue Q Y, Bertilsson L, Sjoqvist F, Ingelman-Sundberg M. Genetic analysis of the Chinese cytochrome P4502D locus: characterization of variant CYP2D6 genes present in subjects with diminished capacity for debrisoquine hydroxylation: Mol Pharmacol 1994 September; 46(3):452-9; Dahl M L, Yue Q Y, Roh H K, Johansson I, Sawe J, Sjoqvist F, Bertilsson L. Genetic analysis of the CYP2D locus in relation to debrisoquine hydroxylation capacity in Korean, Japanese and Chinese subjects. Pharmacogenetics 1995 June; 5(3):159-64; Jaanson P, Marandi T, Kiivet R A, Vasar V, Vaan S, Svensson J O, Dahl M L. Maintenance therapy with zuclopenthixol decanoate: associations between plasma concentrations, neurological side effects and CYP2D6 genotype. Psychopharmacology (Berl) 2002 June; 162(1):67-73; Bertilsson L, Dahl M L, Dalen P, Al-Shurbaji A. Molecular genetics of CYP2D6: clinical relevance with focus on psychotropic drugs. Br J Clin Pharmacol 2002 February; 53(2): 111-22).

In one study, blood samples were collected from 128 individuals according to the pharmacogenetics protocol and after the consent of patients. The DNA was extracted from whole blood by Covance using the PUREGENE DNA isolation kit (D-50K). (U.S. Pat. No. 8,586,610)

In this study, genotypes for the CYP2D6G1846A polymorphism were ascertained for 123 of the 128 consenting individuals, while genotypes for the CYP2D6C100T polymorphism were identified for all 128 participants. Genotyping was performed on amplified DNA fragments. The CYP2D6 genomic region was amplified using a triplex PCR strategy (Neville 2002).

In this study, amplification was performed on 40-100 ng of genomic DNA using a GC-rich PCR kit (Roche Diagnostics, Mannheim, Germany) according to the manufacturer's recommendations. Thermocycling conditions were as follows: initial denaturation (3 min 95° C.), 10 cycles of 30 s of denaturation (30 s at 95° C.), annealing (30 s at 66° C.), and extension, (60 s at 72° C.) followed by 22 cycles: 30 s at 95° C., 30 s at 66° C., 60 s+5 s/cycle at 72° C. A final extension followed (7 min at 72° C.). (U.S. Pat. No. 8,586,610)

In this study, third Wave Technologies, Inc (Madison, Wis.) developed the probe sets for genotyping. Genotyping was performed on PCR products using the Invader® assay (Lyamichev 1999) (Third Wave Technologies, Inc) according to the manufacturer's recommendations. (U.S. Pat. No. 8,586,610)

The study reported the genotyping results of 74 of the study participants. Of these participants, 57 were the CC genotype, 14 were the CT genotype, and 3 were the TT genotype of the CYP2D6C100T polymorphism. The TT and CT genotypes of the CYP2D6C100T polymorphism were determined to include poor CYP2D6 metabolizers. For the CYP2D6G1846A polymorphism, 2 participants were of the AA genotype, 14 participants were of the AG genotype, and 55 participants were of the GG phenotype. The AA and AG genotypes were determined to represent poor CYP2D6 metabolizers. (U.S. Pat. No. 8,586,610)

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, Hitting (including self), Kicking, Grabbing onto people, Pushing, Throwing things, Biting, Scratching, Spitting, Hurting self or others, Tearing things or destroying property, Making physical sexual advances, Pacing, aimless wandering, Inappropriate dress or disrobing, Trying to get to a different place, Intentional falling, Eating/drinking inappropriate substances, Handling things inappropriately, Hiding things, Hoarding things, Performing repetitive mannerisms, General restlessness, Screaming, Making verbal sexual advances, Cursing or verbal aggression, Repetitive sentences or questions, Strange noises (weird laughter or crying), Complaining, Negativism, Constant unwarranted request for attention or help.

Schizophrenia may treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, *cannabis* (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplegia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

The term "treating" or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

Example 1

In 3 poor metabolizers, administration of 105 mg of bupropion hydrochloride and 45 mg of dextromethorphan hydrobromide twice a day resulted in an approximate 3-fold and 3.4-fold increase in dextromethorphan $C_{max}$ and $AUC_{0-12}$, respectively, compared to extensive metabolizers.

By way of comparison, Flesher (WO 2009/006194, p. 86, Table IV) reported that 7 days of twice-daily dosing of 30 mg of dextromethorphan and 30 mg of quinidine resulted in the $C_{max}$ and $AUC_{0-12}$ of poor metabolizers to be increased only about 1.43-fold and 1.46-fold, respectively, compared to extensive metabolizers.

Example 2

An analysis of steady state pharmacokinetic data in 12 poor metabolizers treated with 105 mg of bupropion hydrochloride and 45 mg of dextromethorphan hydrobromide twice a day in efficacy clinical trials showed plasma concentrations of dextromethorphan that were generally higher than exposures for non-poor metabolizer.

Example 3

The properties of a tablet containing a combination of dextromethorphan hydrobromide, which is an uncompetitive NMDA receptor antagonist and sigma-1 receptor agonist, and bupropion hydrochloride, which is an aminoketone and CYP450 2D6 inhibitor, were studied.

The tablets are for oral administration and are round bilayer tablets. Each tablet contains 45 mg dextromethorphan hydrobromide (equivalent to 32.98 mg of the dextromethorphan free base) in an immediate-release formulation and 105 mg bupropion hydrochloride (equivalent to 91.14 mg of the bupropion free base) in an extended-release formulation. Each tablet contains the following inactive ingredients: carbomer homopolymer, colloidal silicon dioxide, crospovidone, glyceryl monocaprylocaprate, L-cysteine hydrochloride monohydrate, magnesium stearate, microcrystalline cellulose, polyvinyl alcohol, red iron oxide, sodium lauryl sulfate, stearic acid, talc, titanium dioxide, and yellow iron oxide.

The effects of renal impairment, hepatic impairment, and CYP2D6 poor metabolizer status on the exposure to a tablet containing 45 mg of dextromethorphan hydrobromide and 105 mg of bupropion hydrochloride are summarized in FIG. 1.

Results depicted in FIG. 1 are based on plasma concentrations in human patients after 8 days of twice daily dosing of a tablet containing 45 mg of dextromethorphan hydrobromide and 105 mg of bupropion hydrochloride. Data are GMRs and 90% CIs. Reference used are the matched healthy subjects for renal and hepatic impairment studies, and extensive or ultra-extensive CYP2D6 metabolizers. AUC represents the area under the plasma concentration-time curve from zero to 12 hours; BUP represents bupropion; CI is confidence interval; $C_{max}$ is maximum plasma concentration; DM represents dextromethorphan; GMRs represents geometric mean ratios; PK represents pharmacokinetics.

For CYP2D6 poor metabolizers, a 3.40-fold increase in dextromethorphan $AUC_{0-12}$ and a 3.00-fold increase in dextromethorphan $C_{max}$ were observed. No significant change was observed in bupropion $AUC_{0-12}$ or bupropion $C_{max}$.

Based upon these results, dosage adjustment is recommended in patients known to be poor CYP2D6 metabolizers because these patients have higher dextromethorphan concentrations than extensive/intermediate CYP2D6 metabolizers. The recommended dosage for patients known to be poor CYP2D6 metabolizers is one tablet once daily, such as in the morning.

The invention claimed is:

1. A method of treating major depressive disorder in a CYP2D6 poor metabolizer comprising, selecting a human patient known to be a poor CYP2D6 metabolizer who is experiencing major depressive disorder, and administering, once daily in the morning for at least two weeks to the human patient, a dosage form containing 1 mg to 105 mg of bupropion hydrochloride, or a molar equivalent amount of the free base or another salt form of bupropion and 1 mg to 45 mg of dextromethorphan hydrobromide, or a molar equivalent amount of the free base or another salt form of dextromethorphan, wherein the dextromethorphan $AUC_{0-12}$ of the human patient is increased 208% to 557% compared to extensive or ultra-extensive CYP2D6 metabolizers.

2. The method of claim 1, wherein the dextromethorphan $AUC_{0-12}$ of the human patient is increased 340% compared to extensive or ultra-extensive CYP2D6 metabolizers.

3. The method of claim 1, wherein approximately 26% of the dextromethorphan is excreted unchanged in the urine of the human patient.

4. The method of claim 1, wherein a combination of 105 mg of bupropion hydrochloride and 45 mg of dextromethorphan hydrobromide is present in a solid dosage form.

5. The method of claim 1, wherein once-daily administration for 8 days avoids the human patient having an about 3.4-fold increase in the $AUC_{0-12}$ of dextromethorphan as compared to the $AUC_{0-12}$ of dextromethorphan that would result after 8 days of twice daily administration of the dosage form to a human patient who is an extensive or ultra-extensive CYP2D6 metabolizer.

6. The method of claim 1, wherein once-daily administration for 8 days avoids the human patient having an about 3-fold increase in the $C_{max}$ of dextromethorphan as compared to the $C_{max}$ of dextromethorphan that would result after 8 days of twice daily administration of the dosage form to a human patient who is an extensive or ultra-extensive CYP2D6 metabolizer.

7. The method of claim 1, wherein the dextromethorphan is in an immediate-release formulation.

8. The method of claim 7, wherein the bupropion is in an extended-release formulation.

9. The method of claim 1, wherein the dosage form further contains a carbomer homopolymer and colloidal silicon dioxide.

10. The method of claim 1, wherein the dosage form further contains crospovidone and glyceryl monocaprylocaprate.

11. The method of claim 1, wherein the dosage form further contains L-cysteine hydrochloride monohydrate.

12. The method of claim 1, wherein the dosage form further contains magnesium stearate and microcrystalline cellulose.

13. The method of claim 1, wherein the dosage form further contains polyvinyl alcohol and sodium lauryl sulfate.

14. The method of claim 1, wherein the dosage form further contains red iron oxide and stearic acid.

15. The method of claim 1, wherein the dosage form further contains talc, titanium dioxide, or yellow iron oxide.

16. The method of claim 1, wherein twice-daily administration of the dosage form to the human patient for 8 days would result in the human patient having about same $AUC_{0-12}$ of bupropion as compared to the $AUC_{0-12}$ of bupropion that would result after 8 days of twice daily administration of the dosage form to a human patient who is an extensive or ultra-extensive CYP2D6 metabolizer.

17. The method of claim 1, wherein twice-daily administration of the dosage form to the human patient for 8 days would result in the human patient having about same $C_{max}$ of bupropion as compared to the $C_{max}$ of bupropion that would result after 8 days of twice daily administration of the dosage form to a human patient who is an extensive or ultra-extensive CYP2D6 metabolizer.

18. A method of treating major depressive disorder in a CYP2D6 poor metabolizer comprising, selecting a human patient known to be a poor CYP2D6 metabolizer who is experiencing major depressive disorder, and administering, once daily in the morning for at least four weeks to the human patient, a dosage form containing 1 mg to 105 mg of bupropion hydrochloride, or a molar equivalent amount of the free base or another salt form of bupropion and 1 mg to 45 mg of dextromethorphan hydrobromide, or a molar equivalent amount of the free base or another salt form of dextromethorphan, wherein the dextromethorphan $AUC_{0-12}$ of the human patient is increased 208% to 557% compared to extensive or ultra-extensive CYP2D6 metabolizers.

19. The method of claim 18, wherein the dextromethorphan $AUC_{0-12}$ of the human patient is increased 340% compared to extensive or ultra-extensive CYP2D6 metabolizers.

20. The method of claim 18, wherein approximately 26% of the dextromethorphan is excreted unchanged in the urine of the human patient.

21. The method of claim 18, wherein the dextromethorphan is in an immediate-release formulation.

22. The method of claim 21, wherein the bupropion is in an extended-release formulation.

23. The method of claim 18, wherein the dosage form further contains a carbomer homopolymer and colloidal silicon dioxide.

24. The method of claim 18, wherein the dosage form further contains crospovidone and glyceryl monocaprylocaprate.

25. The method of claim 18, wherein the dosage form further contains L-cysteine hydrochloride monohydrate.

26. The method of claim 18, wherein the dosage form further contains magnesium stearate and microcrystalline cellulose.

27. The method of claim 18, wherein the dosage form further contains polyvinyl alcohol and sodium lauryl sulfate.

28. The method of claim 18, wherein the dosage form further contains red iron oxide and stearic acid.

* * * * *